(12) United States Patent
You et al.

(10) Patent No.: US 6,891,067 B2
(45) Date of Patent: May 10, 2005

(54) OPTICAL POLYIMIDE PRECURSOR, OPTICAL POLYIMIDE COMPOUND AND FABRICATING METHOD THEREOF

(75) Inventors: Kyung-Hee You, Seoul (KR);
Kwan-Soo Han, Seoul (KR);
Tae-Hyung Rhee, Sungnam-shi (KR);
Eun-Ji Kim, Seoul (KR); Jung-Hee Kim, Seoul (KR); Woo-Hyeuk Jang, Yongin-shi (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 39 days.

(21) Appl. No.: 10/265,705

(22) Filed: Oct. 8, 2002

(65) Prior Publication Data

US 2003/0065128 A1 Apr. 3, 2003

Related U.S. Application Data

(62) Division of application No. 09/799,665, filed on Mar. 7, 2001, now Pat. No. 6,486,292.

(30) Foreign Application Priority Data

Mar. 7, 2000 (KR) ........................................ 2000-11259

(51) Int. Cl.⁷ ...................... C07C 209/36; C08G 73/10; C08G 69/26; G02B 6/00
(52) U.S. Cl. ...................... 564/417; 528/170; 528/125; 528/128; 528/172; 528/173; 528/176; 528/179; 528/183; 528/185; 528/188; 528/220; 528/229; 528/350; 528/353; 528/174; 385/141; 385/142; 385/143; 385/144; 385/145; 564/315; 564/443; 568/586
(58) Field of Search ................. 564/315, 417, 564/443; 568/586

(56) References Cited

U.S. PATENT DOCUMENTS 5,296,635 A * 3/1994 Kase et al. .................. 568/30

FOREIGN PATENT DOCUMENTS

| JP | 59-189122 | 10/1984 |
|----|-----------|---------|
| JP | 10-152559 | 6/1998 |
| JP | 2000-297067 | 10/2000 |

* cited by examiner

Primary Examiner—Peter O'Sullivan
(74) Attorney, Agent, or Firm—Robert E. Bushnell, Esq.

(57) ABSTRACT

The present invention provides an optical polyimide precursor for use in making a polyimide. The precursor is defined by the following formula:

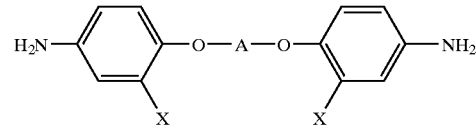

wherein X is Cl, Br, oxo-halide, or fully halogenated alkyl, and A is a divalent aromatic or halogenated aromatic moiety. The present invention provides a method of preparing a diamine compound for use as an optical polyimide precursor. The method includes the steps of dissolving 2-chloro-5-nitrobenzotrifluoride and a diol in N,N-dimethylacetamide to form a solution, adding potassium carbonate, tert-butylammonium chloride and copper powder to said solution and heating the resulting mixture, removing the copper, precipitating and recrystallizing a dinitro-compound resulting from heating the mixture, and dissolving the dinitro-compound and reducing the dinitro-compound to yield a diamine compound.

15 Claims, 2 Drawing Sheets

OPTICAL POLYIMIDE PRECURSOR, OPTICAL POLYIMIDE COMPOUND AND FABRICATING METHOD THEREOF

CROSS-REFERENCE TO RELATED APPLICATIONS

This application is a divisional application of U.S. patent application Ser. No. 09/799,665 filed on 7 Mar. 2004 now U.S. Pat. No. 6,486,292. This related application is relied on and incorporated herein by references in its entirety.

CLAIM OF PRIORITY

This application claims priority to an application entitled "*Optical Polyimide Monomer, Optical Polyimide Compound, and Fabricating Method Thereof*", filed in the Korean Industrial Property Office on 7 Mar. 2000 and assigned Serial No. 2000-11259, the contents of which are hereby incorporated by reference.

BACKGROUND OF THE INVENTION

1. Field of the Invention

The present invention relates generally to an optical linear polymer material, and more particularly, to an optical polyimide precursor, an optical polyimide compound, and the fabricating methods thereof.

2. Description of the Related Art

Generally, optical linear high polymer materials are useful in a variety of optical devices that are the very core of the next-generation fast and large scale data communication industries. Such an optical linear high polymer material is typically utilized in fabricating optical devices for use purpose of optical wave direction, including opto-electronic integrated circuits (OEICs), optical-electrical mixed wiring boards, hydride integration devices, multi-chip-module (MCM) devices, plastic optical fibers, etc.

Of the commercially available optical linear high polymer materials, inorganic crystals such as lithium niobate ($LiNbO_3$) are well known and frequently used. Although widely used as a useful material of various optical devices, inorganic crystals have a limitation in mass production because of difficulties in preparation and processing.

Currently, organic high polymer materials that are feasible for flexible design and processing are under consideration to solve the problem with the inorganic materials. Among the organic high polymer materials, polyimides have been conventionally used as protective buffer agents for semiconductors due to their superior thermal and mechanical properties. An approach to making use of polyimides as an optical polymer material while reducing absorption loss involves substitution of fluorine or deuterium for hydrogen in C—H bonds of the polyimides. High polymer materials typically absorb light in the near infrared region ranging from 1000 nm to 1700 nm. Such an absorption loss results from harmonic overtones at high frequencies caused by stretching and deformation vibrations of C—H bonds in the main chain of the polymer. In an attempt to reduce absorption loss, the hydrogen of C—H bonds is substituted with fluorine or deuterium and the absorption wavelength is thereby shifted out of the near infrared region.

Deuterium-substituted polyimides are not suitable as a material for optical communication devices due to absorption occurring at 1550 nm, whereas fluorine-substituted polyimides are now exploited as a promising material for optical communication devices because they enable minimization of absorption loss at 1000 to 1700 nm. In view of providing a difference in refractive index between core and clad layers, the fabrication of an optical wave guide using the fluorine-substituted polyimide usually involves copolymerization of fluorine-containing monomers with fluorine-free monomers at an appropriate mixing ratio in forming core and clad layers.

However, the related art fluorine-substituted polyimides, i.e., the fluorinated polyimides, have a low refractive index due to the fluorines included therein and their use for the core layer results in a narrower selection range of the material for the clad layer, which must have a lower refractive index than the core layer. Use of the fluorinated polyimides for the clad layer also prevents a problem of increasing absorption loss because the number of C—H bonds increases with the reduced fluorine content.

Furthermore, the related art polyimides have a flexible chain structure with less double refraction (birefringence) so that when the etching depth is large during an etching process, a crack occurs in the thin film due to a difference in the coefficient of thermal expansion between a silicon substrate and the polyimides.

Examples of polyimides of the contemporary art are seen in the following U.S. Patents. U.S. Pat. No. 4,385,165, to Ahne et al., entitled *POLYIMIDE, POLYIDSOINDOLO-QUINAZOLINE DIONE, POLYOXAZINE DIONE AND POLYQUINAZOLINE DIONE PRECURSOR STAGES AND THE MANUFACTURE*, describes oligomeric and polymeric radiation-reactive precursor stages of polyimides.

U.S. Pat. No. 4,988,795, to Uekita et al, entitled *AMPHIPHILIC POLYIMIDE PRECURSOR AND PROCESS FOR PREPARING THE SAME FROM FATTY-SUBSTITUTED POLYAMIDE-ACIDS*, describes amphiphilic polyimide precursors for the preparation of Langmuir-Blodgett films.

U.S. Pat. No. 5,094,517, to Franke, entitled *POLYIMIDE WAVEGUIDES AS OPTICAL SENSORS*, describes waveguides made by coating polyimide on a substrate.

U.S. Pat. No. 5,171,829, to Uekita et al., entitled *COPOLYMERIC AND AMPHIPHILIC POLYIMIDE PRECURSOR, PROCESS FOR PREPARING THE SAME AND THIN FILM*, discloses copolymeric amphiphilic polyimide precursors.

U.S. Pat. No. 5,449,741, to Ando et al., entitled *POLYIMIDE OPTICAL MATERIAL*, describes polyimides with perfluorinated repeating groups.

However, the polyimides disclosed in these patents do not address the problem of achieving appropriate refractive index properties while avoiding cracking when the polyimides are used in thin film applications.

SUMMARY OF THE INVENTION

It is therefore an object of the present invention to provide improved optical polyimides and a fabricating method thereof.

It is a further object of the present invention to provide an improved precursor for preparation of optical polyimides.

A yet further object of the invention is to provide an optical polyimide which has low absorption loss between 1300 and 1500 nm.

A still further object of the invention is to provide an optical polyimide which has high heat resistance.

A still yet further object of the invention is to provide an optical polyimide suitable for use as the core and cladding layers in optical thin film devices.

Another object of the invention is to provide an optical polyimide which can readily be formulated in a wide range of refractive index values.

Yet another object of the invention is to provide an optical polyimide which has low double refraction.

Still another object of the invention is to provide an optical polyimide which does not crack due to thermal expansion coefficient differences during etching of a thin film of the polyimide.

To achieve the above objects, the present invention provides a polyimide precursor, which is a diamine compound, and a polyimide compound for use as an optical high polymer material, and fabricating methods thereof.

The polyimide precursor of the present invention is designed to prevent a crack in the thin film caused by a difference in the coefficient of thermal expansion between a silicon substrate and polyimide as the etching depth becomes larger during an etching process in preparation of the polyimide compound.

The polyimide compound of the present invention is prepared by dissolving the above polyimide precursor and a dianhydride in a solvent to synthesize a polyamic acid as an intermediate, coating the polyamic acid on a silicon substrate, and subjecting the coated silicon substrate to heat treatment.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE PREFERRED EMBODIMENTS

A preferred embodiment of the present invention will be described below with reference to the accompanying drawings. In the following description, well-known functions or constructions are not described in detail.

The present invention is directed to an optical polyimide precursor, an optical polyimide compound, and fabricating methods thereof for use purpose in the field of optical communication. Now, descriptions will be made of the present invention of an optical polyimide precursor and the fabricating method thereof, and then of an optical polyimide compound obtained from the polyimide precursor and the fabricating method thereof.

1. Polyimide Precursor and its Preparation

A polyimide precursor, or diamine compound, of the present invention is contrived to prevent a crack in the thin film resulting from a difference in the coefficient of thermal expansion between a silicon substrate and polyimide as the etching depth becomes larger during an etching process in preparation of a polyimide compound.

The polyimide precursor of the present invention is defined by the formula 1:

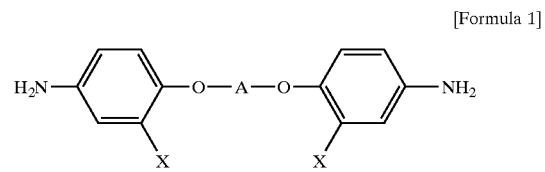

[Formula 1]

wherein X is Cl, Br, oxo-halide, or fully halogenated alkyl, and A is a divalent aromatic or halogenated aromatic moiety. That is, A is a species forming two bonds as shown, and may have a single aromatic ring, or may be a polycyclic aromatic or heteroaromatic.

Figure 1:
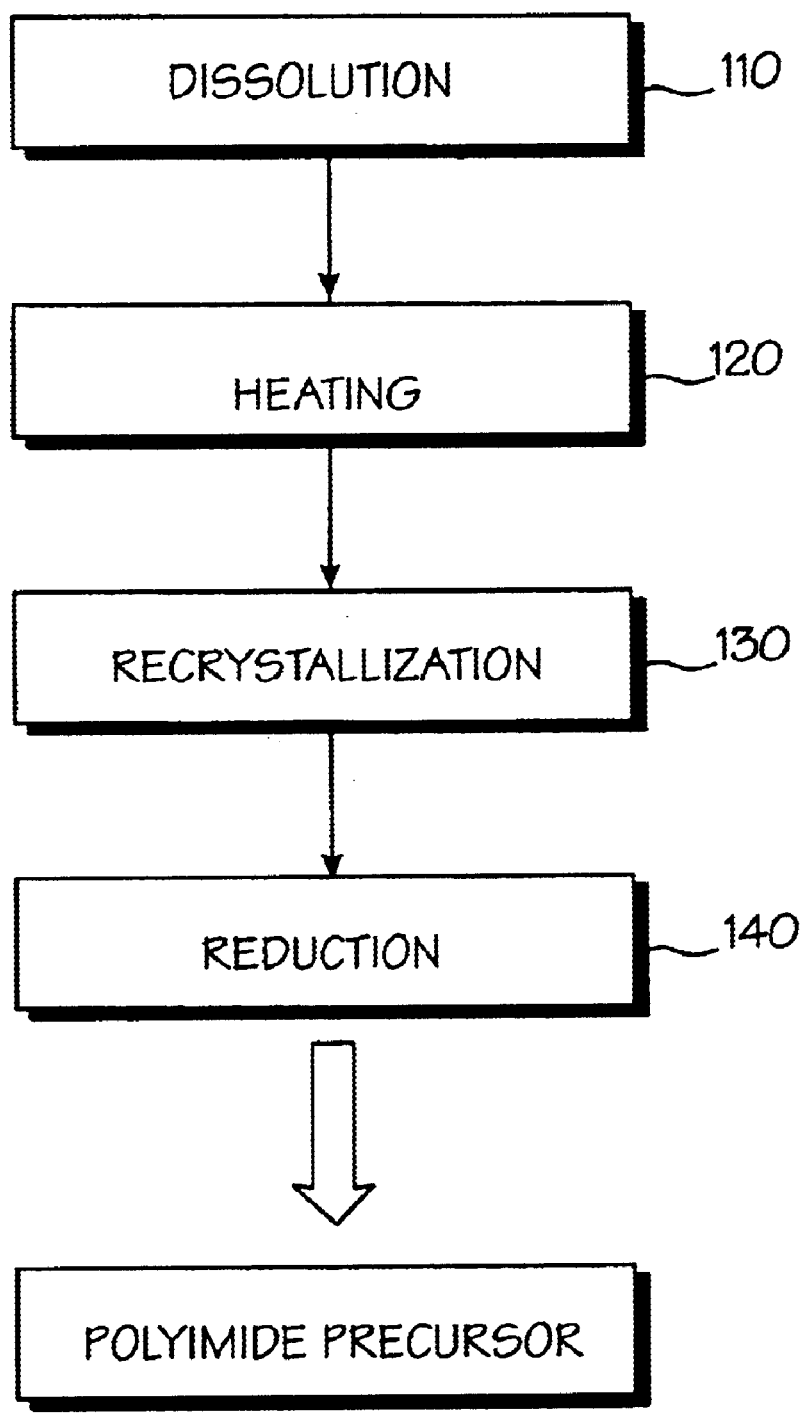
FIG. 1 is a flow chart illustrating a method for preparing polyimide precursors in accordance with an embodiment of the present invention.

FIG. 1 is a flow chart illustrating a method for preparing polyimide precursors according to an embodiment of the present invention. As shown in FIG. 1, the preparation method includes the steps of dissolution 110, heating 120, recrystallization 130 and reduction 140.

For example, when X is $CF_3$, the dissolution step 110 involves dissolving a diol and 2-chloro-5-nitrobenzotrifluoride in N,N-dimethylacetamide(DMAc). Examples of the diol include 2,2-bis(4-hydroxyphenyl)-1,1,1,3,3,3-hexafluoropropane, tetrafluoro-1,4-hydroquinone, tetrachloro-1,4-hydroquinone, hydroquinone, and 4,6-dichlororesorcinol.

The heating step 120 involves adding potassium carbonate, tert-butyl ammonium chloride (TBAC) and copper powder to the reaction mixture of the dissolution step 110 and heating the resulting mixture. The temperature and the time for the heating step 120 vary depending on embodiments of the present invention.

The recrystallization step 130 removes copper from the mixture of the heating step 120 and causes precipitation, after which the precipitate is subjected to recrystallization in acetic acid to yield a dinitro-compound. The solvent in the precipitation depends on the type of the diol used in the dissolution step 110. For example, the solvent can be a mixture of methanol and water (1:1) when the diol is 2,2-bis(4-hydroxyphenyl)-1,1,1,3,3,3-hexafluoropropane, tetrafluoro-1,4-hydroquinone, or hydroquinone; concentrated sulfuric acid when the diol is tetrachloro-1,4-hydroquinone; or a mixture of water and hydrochloric acid when the diol is 4,6-dichlororesorcinol.

In the reduction step 140, the dinitro-compound is dissolved in tetrahydrofuran and then reduced using a catalyst to yield a diamine compound which is the polyimide precursor. This step 140 is performed under hydrogen atmosphere and the catalyst is palladium. The palladium and hydrogen reduce the $-NO_2$ groups to $-NH_2$.

The polyimide precursor of the present invention can solve the problem that the core and clad layers composed of the polyimide compound made from the polyimide precursor differ from each other in double refraction. The polyimide precursor also enables the control of refractive index in a wide range through substitution with halogenated aromatic rings in the aromatic moiety of the formula 1, and thereby, permits more liberal selection of a material for the core and clad layers.

The following embodiments 1-1 through 1-5 illustrate the synthesis of five different polyimide precursor compounds of the present invention, as shown in Formula 1 with X being $CF_3$.

Embodiment 1-1

2,2-bis(4-hydroxyphenyl)-1,1,1,3,3,3-hexafluoropropane (5.1 g, 0.0152 mol) and 2-chloro-5-nitrobenzotrifluoride (7.518 g, 0.0333 mol) were dissolved in 63 ml of N,N-dimethylacetamide (with about 20% solid content). To the reaction mixture were added 6.91 g of potassium carbonate (0.05 mol), 0.0975 g of tert-butyl ammonium chloride and 0.195 g of copper powder, after which the mixture was heated at 100° C. for 2 hours and filtered to remove copper. The filtrate was then added to a mixed solvent of methanol and water (1:1), resulting in precipitation. Recrystallization from acetic acid gave dinitro-compound as yellow crystals (8.497 g, 78.5% yield). 5.0 g of this compound was dissolved in tetrahydrofuran and reduced using palladium (10% in activated carbon) as a catalyst under hydrogen atmosphere, to obtain a diamine compound defined by the formula 1 (2.633 g, 60.0% yield).

Embodiment 1-2

Tetrafluoro-1,4-hydroquinone (2.761 g, 0.0152 mol) and 2-chloro-5nitrobenzotrifluoride (7.518 g, 0.0333 mol) were dissolved in 51 ml of N,N-dimethylacetamide (with about 20% solid content). To the reaction mixture were added 6.91 g of potassium carbonate (0.05 mol), 0.0975 g of tert-butyl ammonium chloride and 0.195 g of copper powder, after which the mixture was heated at 110° C. for 16 hours and filtered to remove copper. The filtrate was then added to a mixed solvent of methanol and water (1:1), resulting in precipitation. Recrystallization from acetic acid gave dinitro-compound as flesh-colored crystals (5.505 g, 64.8% yield). 5.0 g of this compound was dissolved in tetrahydrofuran and reduced using palladium (10% in activated carbon) as a catalyst under hydrogen atmosphere, to obtain a diamine compound defined by the formula 1 (3.407 g, 76.3% yield).

Embodiment 1-3

Tetrachloro-1,4-hydroquinone (3.768 g, 0.0152 mol) and 2-chloro-5nitrobenzotrifluoride 7.518 0.0333 mol) were dissolved in 56 ml of N,N-dimethylacetamide (with about 20% solid content). To the reaction mixture were added 6.91 g of potassium carbonate (0.05 mol), 0.0975 g of tert-butyl ammonium chloride and 0.1958 of copper powder, after which the mixture was heated at 80° C. for 24 hours and filtered to remove copper. The filtrate was then added to concentrated sulfuric acid, resulting in precipitation. Recrystallization from acetic acid gave dinitro-compound as yellow crystals (5.90 g, 62.0% yield). 5.0 g of this compound was dissolved in terrahydrofuran and reduced using palladium (10% in activated carbon) as a catalyst under hydrogen atmosphere, to obtain a diamine compound defined by the formula 1 (3.148 g, 69.6% yield).

Embodiment 1-4

Hydroquinone (1.6711 g, 0.0152 mol) and 2-chloro-5-nitrobenzotrifluoride (7.518 g, 0.0333 mol) were dissolved in 46 ml of N,N-dimethylacetamide (with about 20% solid content). To the reaction mixture were added 6.91 g of potassium carbonate (0.05 mol), 0.0975 g of tert-butyl ammonium chloride and 0.195 g of copper powder, after which the mixture was heated at 110° C. for 3 hours and filtered to remove copper. The filtrate was then added to a mixed solvent of methanol and water (1:1), resulting in precipitation. Recrystallization from acetic acid gave dinitro-compound as yellow crystals (5.337 g, 71.9% yield). 5.0 g of this compound was dissolved in tetrahydrofuran and reduced using palladium (10% in activated carbon) as a catalyst under hydrogen atmosphere, to obtain a diamine compound defined by the formula 1 (3.313 g, 75.5% yield).

Embodiment 1-5

4,6-dichlororesorcinol (2.721 g, 0.0152 mol) and 2-chloro-5-nitrobenzotrifluoride (7.518 g, 0.0333 mol) were dissolved in 46 ml of N,N-dimethylacetamide (with about 20% solid content). To the reaction mixture were added 6.91 g of potassium carbonate (0.05 mol), 0.0975 g of tert-butyl ammonium chloride and 0.195 g of copper powder, after which the mixture was heated at 80° C. for 15 hours and filtered to remove copper. The filtrate was then added to mixed solvent of hydrochloric acid added to water, resulting in precipitation. Recrystallization from acetic acid gave dinitro-compound as yellow crystals (5.287 g, 62.4% yield).

5.0 g of this compound was dissolved in tetrahydrofuran and reduced using palladium (10% in activated carbon) as a catalyst under hydrogen atmosphere, to obtain a diamine compound defined by the formula 1 (2.347 g, 53.5% yield).

2. Polyimide Compounds and Their Preparation (A) Polyimide Compound

A polyimide compound of the present invention is prepared by dissolving the above-prepared polyimide precursor and a dianhydride in a solvent to synthesize an intermediate, polyamic acid, coating the polyamic acid on a silicon substrate, and subjecting the coated silicon substrate to heat treatment. Here, the dianhydride is defined by the formula 2 and the polyimide compound of the present invention is defined by the formula 3.

[Formula 2]

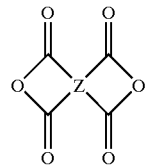

wherein Z is a tetravalent moiety which may be an aromatic ring, a partly/fully fluorinated aromatic ring, a partly/fully chlorinated aromatic ring, a partly/fully fluorinated cycloaliphatic group, a partly/fully chlorinated cycloaliphatic group, a partly/fully fluorinated aliphatic group, a partly/fully chlorinated aliphatic group, or combinations thereof connected via hetero atoms. Here, partly fluorinated or chlorinated means that at least one of the hydrogens of C—H bonds in the moiety is substituted by fluorine or chlorine. Fully fluorinated or chlorinated means that all of the C—H bonds are substituted.

[Formula 3]

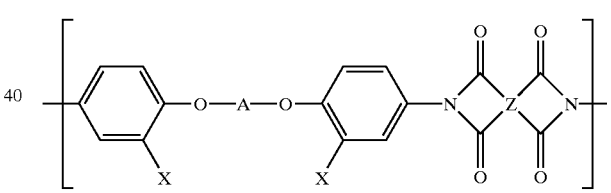

wherein X is Cl, Br, oxo-halide, or fully halogenated alkyl; A is a divalent aromatic or halogenated aromatic moiety; and Z is a tetravalent moiety which may be an aromatic ring, a partly/fully fluorinated aromatic ring, a partly/fully chlorinated aromatic ring, a partly/fully fluorinated cycloaliphatic group, a partly/fully chlorinated cycloaliphatic group, a partly/fully fluorinated aliphatic group, a partly/fully chlorinated aliphatic group, or combinations thereof connected via hetero atoms.

Figure 2:
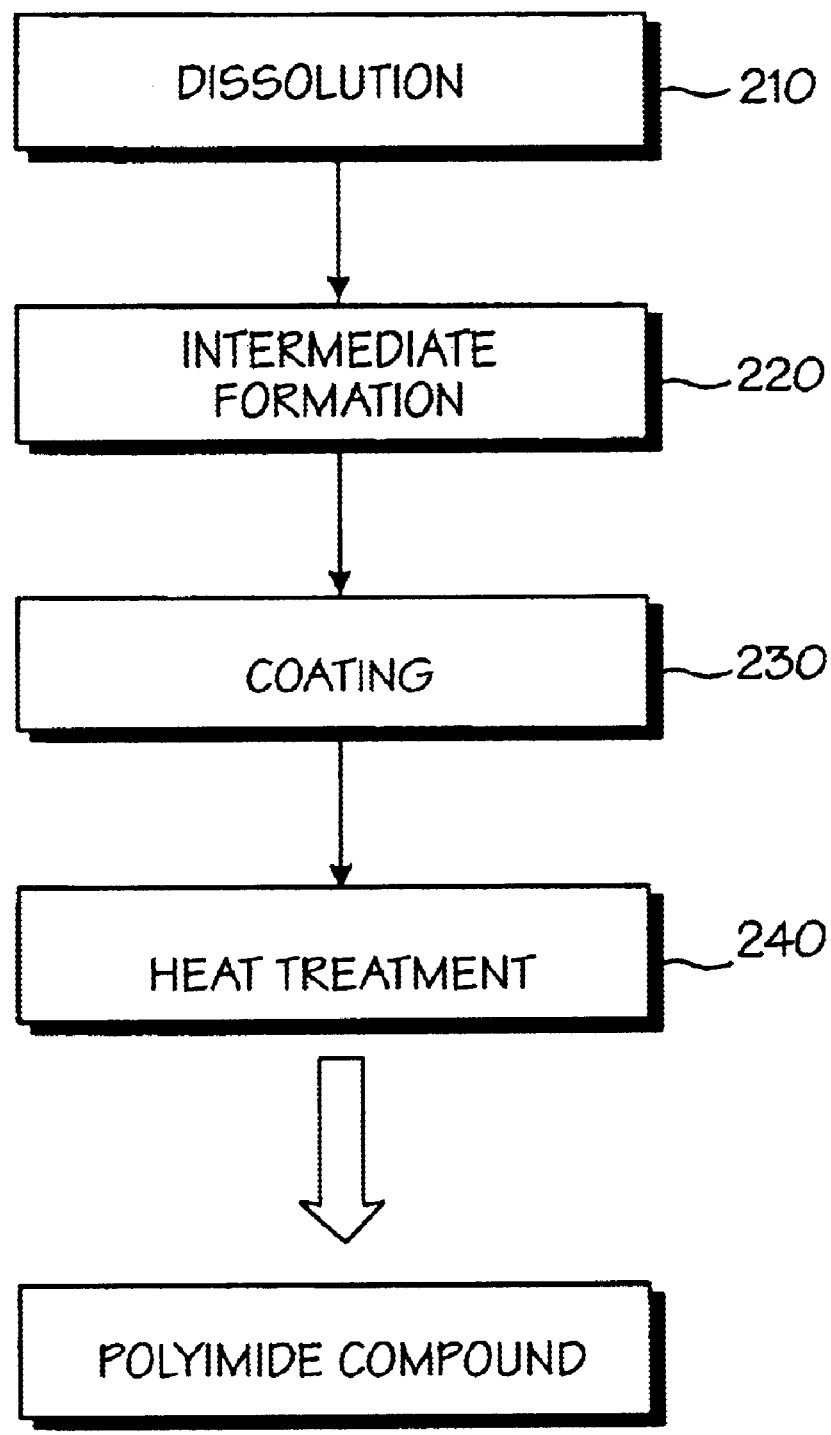
FIG. 2 is a flow chart illustrating a method for preparing polyimide compounds in accordance with an embodiment of the present invention.

FIG. 2 is a flow chart illustrating a method for preparing polyimide compounds according to an embodiment of the present invention. As shown in FIG. 2, the preparation method includes the steps of dissolution 210, intermediate formation 220, coating 230, and heat treatment 240.

The dissolution step 210 involves dissolving the polyimide precursor of the formula 1 and the dianhydride of the formula 2 include 1,4-bis(4-amino-2-trifluoromethylphenoxy)tetrafluorobenzene, 1,4-bis(4-amino-2-trifluoromethylphenoxy)benzene, 1,3-bis(4-amino-2-trifluoromethylphenoxy)-4,6-dichlorobenzene and so forth. Examples of the dianhydride include 2,2-bis(dicarboxyphenyl)hexafluoropropane dianhydride and 1,2,4,5-benzenetetracarboxylic dianhydride.

The intermediate formation step 220 involves stirring the reaction mixture from the dissolution step 210 under nitrogen atmosphere to form an intermediate, polyamic acid. The coating step 230 coats a silicon substrate with the polyamic acid solution from the intermediate formation step 220.

The heat treatment step 240 subjects the silicon substrate coated with the polyamic acid solution to heat treatment so as to finally yield a polyimide compound. The heat treatment 240 is performed under nitrogen atmosphere in an oven, where the nitrogen prevents permeation of water into the polyimide compound and hence chain breakage of the polymer structure.

Embodiments 2-1 through 2-3, shown below, illustrate the preparation of three such polymers based on using 2,2-bis (dicarboxyphenyl)hexafluoropropane dianhydride as the dianhydride.

Embodiment 2-1

1,4-bis(4-amino-2-trifluoromethylphenoxy) tetrafluorobenzene (4.503 g, 0.009 mole) and 2,2-bis (dicarboxyphenyl)hexafluoropropane dianhydride (4 g, 0.009 mole) were dissolved in 42.5 g of dimethylacetamide. The reaction mixture was stirred under nitrogen atmosphere for 24 hours to form polyamic acid, after which the polyamic acid was spin coated on a silicon substrate. The coated silicon substrate was then subjected to heat treatment under nitrogen atmosphere in an oven at 100° C. for 30 mm., at 200° C. for further 1 hour and at 350° C. for still further 1 hour, to yield a transparent polyimide film. As such, the refractive index of the polyimide was 1.5099 in the TE mode and 1.5024 in the TM mode at 1550 nm.

Embodiment 2-2

1,4-bis(4-amino-2-trifluoromethylphenoxy)benzene (3.855 g, 0.009 mole) and 2,2-bis (dicarboxyphenyl) hexafluoropropane dianhydride (4 g, 0.009 mole) were dissolved in 42.5 g of dimethylacetamide. The reaction mixture was stirred under nitrogen atmosphere for 24 hours to form a polyamic acid, after which the polyamic acid was spin coated on a silicon substrate. The coated silicon substrate was then subjected to heat treatment under nitrogen atmosphere in an oven at 100° C. for 30 min., at 200° C. for further 1 hour and at 350° C. for still further 1 hour, to yield a transparent polyimide film. As such, the refractive index of the polyimide was 1.5289 in the TE mode and 1.5224 in the TM mode at 1550 nm.

Embodiment 2-3

1,3-bis(4-amino-2-trifluoromethylphenoxy)-4,6-dichlorobenzene (4.475 g, 0109 mole) and 2,2-bis (dicarboxyphenyl)hexafluoropropane dianhydride (4 g, 0.009 mole) were dissolved in 42.4 g of dimethylacetamide. The reaction mixture was stirred under nitrogen atmosphere for 24 hours to form polyamic acid, after which the polyamic acid was spin coated on a silicon substrate. The coated silicon substrate was then subjected to heat treatment under nitrogen atmosphere in an oven at 100° C. for 30 min., at 200° C. for further 1 hour and at 350° C. for still further 1 hour, to yield a transparent polyimide film. As such, the refractive index of the polyimide was 1.5344 in the TE mode and 1.5303 in the TM mode at 1550 nm.

Embodiments 3-1 through 3-3, shown below, illustrate the preparation of three such polymers based on using 1,2,4,5-benzenetetracarboxylic dianhydride as the dianhydride.

Embodiment 3-1

1,4-bis(4-amino-2-trifluoromethylphenoxy) tetrafluorobenzene (4.503 g, 0.009 mole) and 1,2,4,5-benzenetetracarboxylic dianhydride (1.963 g, 0.009 mole) were dissolved in 32.3 g of dimethylacetamide. The reaction mixture was stirred under nitrogen atmosphere for 24 hours to form polyamic acid, after which the polyamic acid was spin coated on a silicon substrate. The coated silicon substrate was then subjected to heat treatment under nitrogen atmosphere in an oven at 100° C. for 30 min., at 200° C. for further 1 hour and at 350° C. for still further 1 hour, to yield a transparent polyimide film. As such, the refractive index of the polyimide was 1.5397 in the TE mode and 1.5239 in the TM mode at 1550 nm.

Embodiment 3-2

1,4-bis(4-amino-2-trifluoromethylphenoxy)benzene (3.855 g, 0.009 mole) and 1,2,4,5-benzenetetracarboxylic dianhydride (1.963 g, 0.009 mole) were dissolved in 29.1 g of dimethylacetamide. The reaction mixture was stirred under nitrogen atmosphere for 24 hours to form polyamic acid, after which the polyamic acid was spin coated on a silicon substrate. The coated silicon substrate was then subjected to heat treatment under nitrogen atmosphere in an oven at 100° C. for 30 min., at 200° C. for further 1 hour and at 350° C. Or still further 1 hour, to yield a transparent polyimide film. As such, the refractive index of the polyimide was 1.5871 in the TE mode and 1.5513 in the TM mode at 1550 nm.

Embodiment 3-3

1,3-bis(4-amino-2-trifluoromethylphenoxy)-4,6-dichlorobenzene (4.475 g, 0.009 mole) and 1,2,4,5-benzenetetracarboxylic dianhydride (1.963 g, 0.009 mole) were dissolved in 32.3 g of dimethylacetamide. The reaction mixture was stirred under nitrogen atmosphere for 24 hours to form polyamic acid, after which the polyamic acid was spin coated on a silicon substrate. The coated silicon substrate was then subjected to heat treatment under nitrogen atmosphere in an oven at 100° C. for 30 min., at 200° C. for further 1 hour and at 350° C. for still further 1 hour, to yield a transparent polyimide film. As such, the refractive index of the polyimide was 1.5727 in the TE mode and 1.5670 in the TM mode at 1550 nm.

(B) Copolymer Polyimide Compound

The copolymer polyimide compounds of the present invention are prepared by copolymerizing different polyimide precursors of the formula 1 with a dianhydride of the formula 2. Different copolymer polyimides may be prepared by varying the ratio of the polyimide precursors used in the copolymerization. The individual copolymer polyimide compounds thus obtained have different refractive indexes. Thus, a desired refractive index may be achieved by selecting an appropriate ratio of the polyimide precursors.

i) First Series of Copolymer Polyimide Compounds and Their Preparation

The first series of copolymer polyimide compounds according to an embodiment of the present invention are prepared by copolymerizing two different polyimide precursors, e.g., 1,4-bis(4-amino-2-trifluoromethylphenoxy) tetrafluorobenzene, 1,4-bis(4-amino-2-trifluoromethylphenoxy)benzene and 1,3-bis(4-amino-2-trifluoromethylphenoxy)-4,6-dichlorobenzene with 2,2 bis (dicarboxyphenyl)hexafluoropropane dianhydride (6FDA).

These compounds are defined by the formula 4.

[Formula 4]

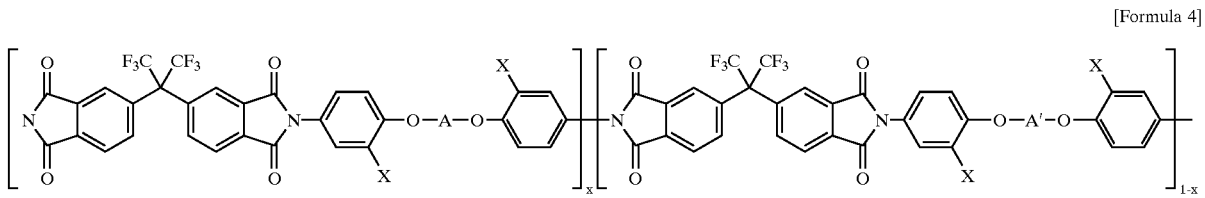

wherein X is Cl, Br, oxo-halide, or fully halogenated alkyl, and A and A' are each independently a divalent aromatic or halogenated aromatic moiety. Here, x and 1-x represent the relative mole fractions of the two copolymeric units in a copolymer having only these two units.

In the preparation method of the first copolymer polyimide compounds, approximately the same amount, in moles, of the polyimide precursor and 2,2-bis(dicarboxyphenyl) hexafluoropropane dianhydride (6FDA) are first dissolved in dimethylacetamide. The reaction mixture is stirred under nitrogen atmosphere to form an intermediate, polyamic acid, which is spin-coated on a silicon substrate. The coated silicon substrate is then subjected to heat treatment in an oven to yield the first copolymer polyimide compounds of the formula 4.

ii) Second Series of Copolymer Polyimide Compound and Their Preparation

Second copolymer polyimide compounds according to an embodiment of the present invention are prepared by copolymerizing one of different polyimide precursors, e.g., 1,4-bis(4-amino-2-trifluoromethylphenoxy)tetrafluorobenzene, 1,4-bis(4-amino-2-trifluoromethylphenoxy)benzene and 1,3-bis(4-amino-2 trifluoromethylphenoxy)-4,6-dichlorobenzene with 1,2,4,5-benzenetetracarboxylic dianhydride, also know as pyromellitic dianhydride (PDMA). These compounds are defined by the formula 5.

amino-2-trifluoromethylphenoxy)benzene (2.506 g, 0.00585 mole) as well as 1,2,5,6-benzenetetracarboxylic dianhydride were dissolved in 30.2 g of dimethylacetamide. The reaction mixture was stirred under nitrogen atmosphere for 24 hours to form polyamic acid, after which the polyamic acid was spin coated on a silicon substrate. The coated silicon substrate was the subjected to heat treatment under nitrogen atmosphere in an oven at 100° C. for 30 min., at 200° C. for further 1 hour and at 350° C. for still further 1 hour, to yield a transparent polyimide film. As such, the refractive index of the polyimide was 1.5597 in the TE mode and 1.5400 in the Tm mode at 1550 nm.

As described above, the optical polyimide precursor, the polyimide compound and the fabricating methods thereof according to the embodiment of the present invention provide the capability of preventing a crack in the thin film during an etching process, while maintaining less absorption loss and high heat resistance of the related art fluorinated polyimide compounds.

The present invention also provides the capability of selecting materials of core and clad layers more liberally by controlling the refractive index in a relatively wide range with less absorption loss at a wavelength for optical communication between 1300 to 1550 nm.

While the invention has been shown and described with reference to a certain preferred embodiment thereof, it will be understood by those skilled in the art that various changes

[Formula 5]

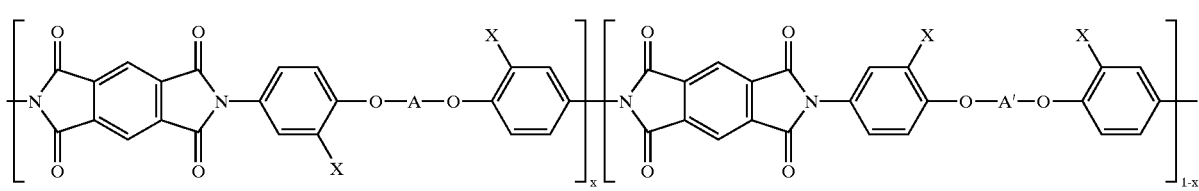

wherein X is Cl, Br, oxo-halide, or fully halogenated alkyl, and A and A' are independently a divalent aromatic or halogenated aromatic moiety. Here, x and 1-x represent the relative mole fractions of the two copolymeric units in a copolymer having only these two units.

In the preparation method of the second copolymer polyimide compounds, the polyimide precursor and 1,2,4,5-benzenetetracarboxylic dianhydride (PDMA) are first dissolved in dimethylacetamide. The reaction mixture is stirred under nitrogen atmosphere to form an intermediate, polyamic acid, which is spin coated on a silicon substrate. The coated silicon substrate is then subjected to heat treatment in an oven to yield the first copolymer polyimide compounds of the formula 5.

Embodiment 3-4 is an example of a copolymer of the second series.

Embodiment 3-4

1,4-bis(4-amino-2-trifluoromethylphenoxy) tetrafluorobenzene (1.576 g, 0.00315 mole) and 1,4-bis(4- in form and details may be therein without departing from the spirit and scope of the invention as defined by the appended claims.

What is claimed is:

1. A method of preparing a diamine compound for use as an optical polyimide precursor, comprising the steps of:
    dissolving 2-chloro-5-nitrobenzotrifluoride and a diol in N,N-dimethylacetamide to form a solution;
    adding potassium carbonate, tert-butylammonium chloride and copper powder to said solution and heating the resulting mixture;
    removing the copper;
    precipitating and recrystallizing a dinitro-compound resulting from heating the mixture; and
    dissolving the dinitro-compound and reducing the dinitro-compound to yield said diamine compound having the formula:

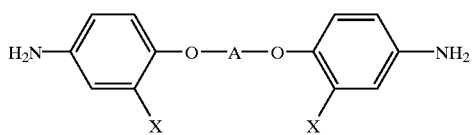

where A represents a divalent aromatic moiety and X is selected from the group consisting of Cl, Br and fully halogenated alkyl.

2. The method of claim 1, said diol being 2,2-bis(4-hydroxyphenyl)-1,1,1,3,3,3-hexafluoropropane.

3. The method of claim 1, said diol being tetrafluoro-1,4-hydroquinone.

4. The method of claim 1, said diol being tetrachloro-1,4-hydroquinone.

5. The method of claim 1, said diol being hydroquinone.

6. The method of claim 1, said diol being 4,6-dichlororesorcinol.

7. The method of claim 1, said diol being tetrafluoro-1,3-hydroquinone.

8. The method of claim 2, wherein a solvent for the precipitating step is a mixture of methanol and water.

9. The method of claim 3, wherein a solvent for the precipitating step is a mixture of methanol and water.

10. The method of claim 4, wherein a solvent for the precipitating step is a concentrated sulfuric acid.

11. The method of claim 5, wherein a solvent for the precipitating step is a mixture of methanol and water.

12. The method of claim 1, the recrystallizing step comprising the step of using acetic acid.

13. The method of claim 1, wherein a solvent for the step of dissolving the dinitro-compound is tetrahydrofuran.

14. The method of claim 1, the removing step further comprising the step of filtering said copper.

15. The method of claim 1, the reducing step further comprising the step of catalyzing a reaction with palladium.

* * * * *